United States Patent [19]

Doring

[11] Patent Number: 4,488,561
[45] Date of Patent: Dec. 18, 1984

[54] PACING LEAD WITH INSERTABLE MEMORY COIL

[75] Inventor: John D. Doring, Spring Lake Park, Minn.

[73] Assignee: Medtronic, Inc., Minneapolis, Minn.

[21] Appl. No.: 507,653

[22] Filed: Jun. 27, 1983

[51] Int. Cl.³ .............................................. A61N 1/36
[52] U.S. Cl. .................................. 128/786; 128/419 P
[58] Field of Search ................... 128/303 R, 784, 785, 128/786, 798, 783, 419 P

[56] References Cited

U.S. PATENT DOCUMENTS 4,136,703 1/1979 Wittkampf ....................... 128/419 P
4,402,330 9/1983 Lindemans .......................... 128/786

Primary Examiner—Lee S. Cohen
Assistant Examiner—Steven Falk
Attorney, Agent, or Firm—Reed A. Duthler; Joseph F. Breimayer; John L. Rooney

[57] ABSTRACT

A body implantable lead which may be provided with a desired predetermined curve. A memory coil is inserted into the lead while straightened by a stylet. After removal of the stylet, the memory coil imparts the desired curve to the lead.

13 Claims, 8 Drawing Figures

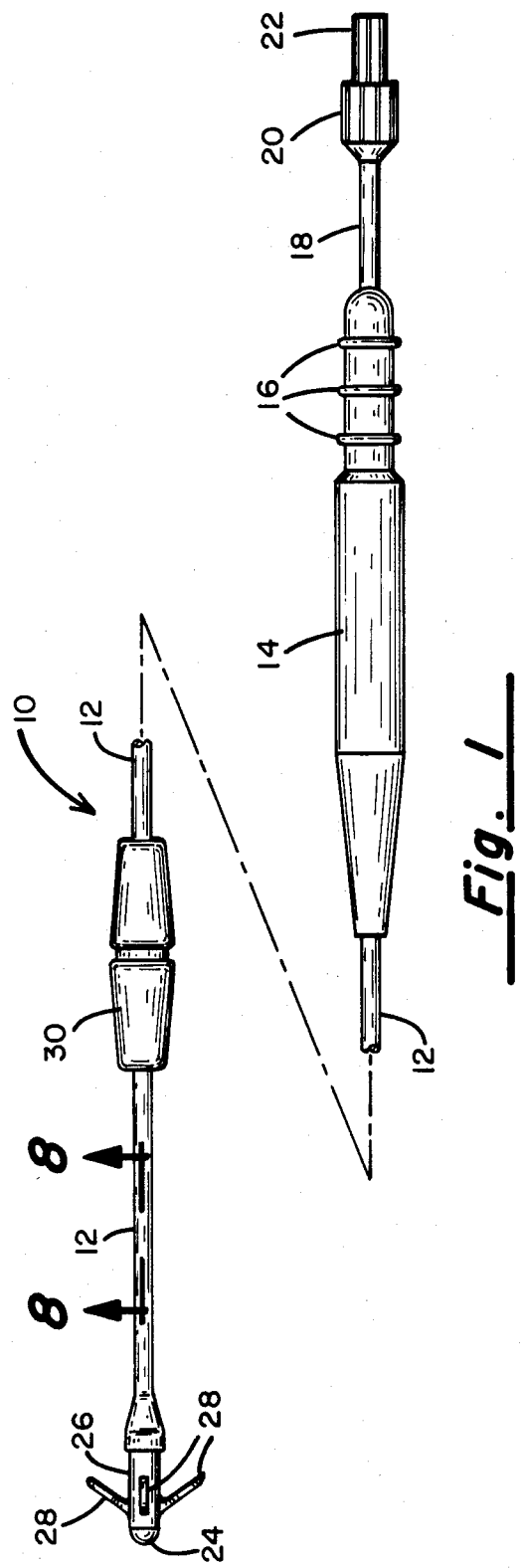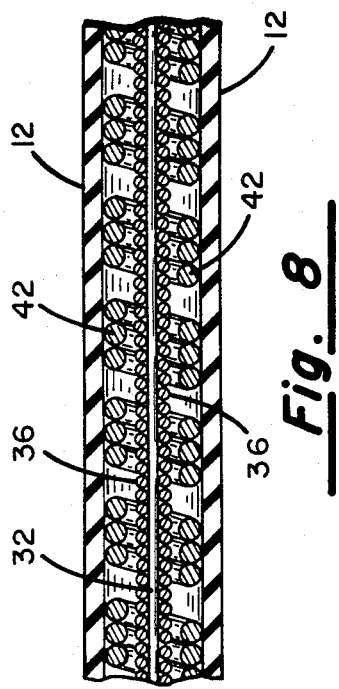

PACING LEAD WITH INSERTABLE MEMORY COIL

BACKGROUND OF THE INVENTION

This invention relates generally to electrical medical leads and, in particular, to cardiac stimulation leads.

In the field of cardiac pacing, there are available pacemakers designed to provide stimulus pulses to and sense the electrical activity of a patient's heart. Typically, leads intended for use in the ventricle employ an essentially straight lead body which allows location of the electrode at the ventricular apex. However, in those applications where the electrode is desired to be located in other areas of the heart, such as the atrium for A-V sequential pacing or the ventricular septum for his bundle monitoring, it is desirable to use a lead which is provided with a curve in its distal portion to direct the electrode to its desired location within the heart. For example, atrial pacing leads may display a J-shaped bend over their distal portion to enable placement of the tip electrode in the atrial appendage of the right atrium, or an L-shaped bend to facilitate placement of the electrode in the coronary sinus.

There have been two general approaches to providing a lead with a desired bend or curve. The most common approach has been to fabricate the lead in such a manner that it tends to assume the desired curve, straightening the lead for insertion by means of a stiffening stylet. In these leads, the curve facilitates the location of the electrode at the desired location. Examples of such leads are discussed in U.S. Pat. No. 3,939,843 issued to Smyth, and U.S. Pat. No. 3,729,008 issued to Berkovits and U.S. Pat. No. 4,332,359 issued to McCorkle. The preset curve of the lead may be also straightened by means of a tubular structure such as a needle or a catheter, as described in U.S. Pat. No. 3,516,412 issued to Ackerman and U.S. Pat. No. 3,866,615 issued to Hewson. As an alternative to providing the lead with a preset curve, some leads are adapted to be used with stylets which temporarily impart a desired curve to the lead. Examples of this technique can be found in U.S. Pat. No. 4,136,703 issued to Wittkampf and in commonly assigned U.S. patent application Ser. No. 306,050 by Williams for a "Positive Anchoring A-V Lead."

SUMMARY OF THE INVENTION

The present invention provides a lead which may be easily provided with a desired predetermined curve or bend. As such, the invention allows for a pacing lead convertible from use in the ventricle to use in the atrium or other desired location. The lead body tends to assume a generally straight configuration, typical of prior art ventricular leads and, if used with a straight stylet typical of the prior art, it may be used in the ventricle. The present invention, however, employs a stylet wire having a generally straight configuration, removably mounted within a concentric memory coil tending to assume the desired curved shape. The stylet and memory coil may be inserted together within the lead body, the stylet maintaining the memory coil in a generally straight configuration. After removal of the stylet, the memory coil urges the lead body to assume the desired predetermined curve, facilitating use of the lead in the atrium. The memory coil may extend for the entire length of the lead, or only for a portion thereof.

The many objects, advantages and novel features of the present invention will become apparent from the following detailed description of the invention when considered in conjunction with the accompanying drawings.

BRIEF DESCRIPTION OF THE DRAWINGS

FIG. 1 shows a side plan view of a pacing lead according to the present invention;

FIG. 8 shows a cross-sectional view of a pacing lead according to the present invention, illustrating the relationship between the lead, the straightening stylet, and the curve-imparting memory coil.

DETAILED DESCRIPTION OF THE DRAWINGS

Figure 2:
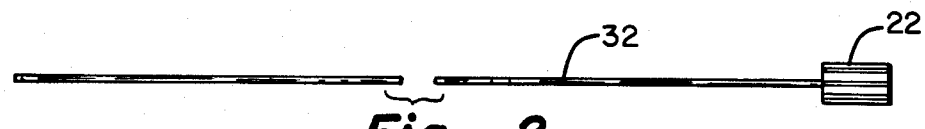
FIG. 2 shows a side plan view of a straightening stylet according to the present invention.

FIG. 1 shows a side plan view of a pacing lead according to the present invention. Elongated lead body 10 is provided with an insulative sheath 12 which extends from the distal end of the lead to the proximal end of the lead. At the proximal end of the lead is located connector assembly 14, which is provided with sealing rings 16, and mounts connector pin 18. Slideably mounted around insulative sheath 12 is anchoring sleeve 30. Anchoring sleeve 30, insulative sheath 12 and connector assembly 14 may conveniently be fabricated of polyurethane or silicone rubber. Connector pin 18 may be fabricated of any conductive metal, and is preferably fabricated of stainless steel. Tine sheath 26 is located at the distal end of lead body 10, and bears four tines 28. Tines 28 are of known design, and are fully described in U.S. Pat. No. 3,902,501, issued to Citron et al. Mounted at the distal tip of lead body 10 is electrode 24. Electrode 24 is coupled to connector pin 18 by means of a conductor coil, not visible in this drawing. Electrode 24 may conveniently be fabricated of platinum or other conductive biocompatible material. Tine sheath 26 may be fabricated of silicone rubber, polyurethane or other suitable non-conductive material. Visible protruding from connector pin 18 are stylet knob 22 and memory coil insertion tool knob 20 (discussed below).

FIG. 2 illustrates a straightening stylet suitable for use with the present invention. Stylet wire 32 is of sufficient length to extend from the proximal end to the distal end of the lead illustrated in FIG. 1. At the proximal end of stylet wire 32 is located stylet knob 22. Stylet wire 32 may be conveniently fabricated of stainless steel and knob 22 may be fabricated of plastic or other suitable material.

Figure 3:
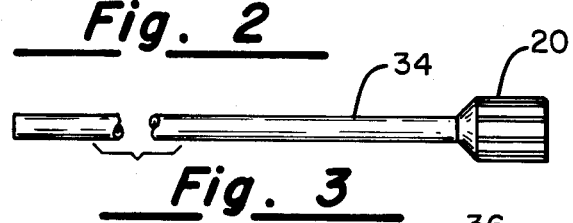
FIG. 3 shows a side plan view of a memory coil insertion tool according to the present invention.

FIG. 3 shows an insertion tool according to the present invention. The insertion tool is comprised of a tubular member 34 which has a longitudinal bore running throughout its length. Mounted at the proximal end of tubular member 34 is knob 20, which also has a central bore, coupled to the bore of tubular member 34. Stylet wire 32 (FIG. 2) is insertable through the bores of knob 20 and tubular member 34. When so inserted, the distal end of stylet wire 32 protrudes from the distal end of tubular member 34 for a significant distance. Tubular member 34 and knob 20 may be fabricated of plastic or any other convenient material. Alternatively, tubular member 34 may take the form of a coil having a central lumen, fabricated of any convenient metal or plastic.

Figure 4:
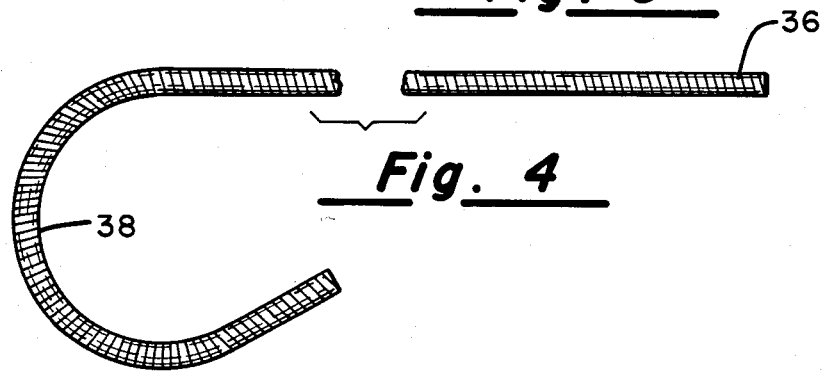
FIG. 4 shows a side plan view of a first embodiment of a memory coil according to the present invention.

FIG. 4 illustrates a side plan view of a memory coil appropriate for use with the present invention. Memory coil 36 is shown as a monofilar coil tending to assume a predetermined bend 38. The length of memory coil 36 corresponds generally to the distance stylet wire 32 protrudes from the distal end of tubular member 34 (FIG. 3) when so inserted. Memory coil 36 has a diameter approximately equal to that of tubular member 34 (FIG. 3), and has a central lumen into which stylet wire 32 (FIG. 2) is insertable. When stylet wire 32 is so inserted, memory coil 36 is substantially straightened, with the result that curve 38 is not displayed.

Figure 5:
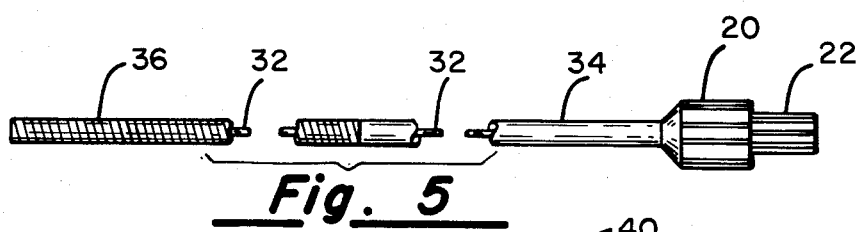
FIG. 5 shows a side plan view of a stylet, memory coil and insertion tool, as assembled, according to the present invention.

FIG. 5 shows the straightening stylet, memory coil insertion tool, as assembled for introduction in to the lead of FIG. 1. In this view, stylet wire 32 is seen to straighten memory coil 36. The insertion tool locates memory coil 36 distal to tubular member 34. The assembly shown in this figure is insertable into the proximal end of the lead shown in FIG. 1, through connector pin 18 which is provided with a central bore, communicating with the lumen of lead body 10.

Figure 6:
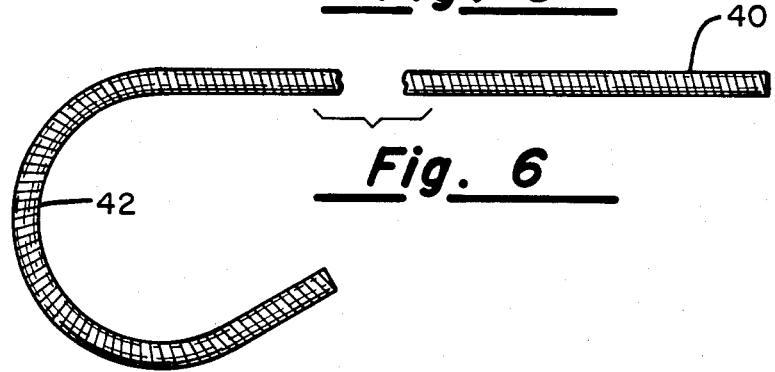
FIG. 6 shows a side plan view of a second embodiment of a memory coil according to the present invention.

FIG. 6 shows an alternate embodiment of a memory coil according to the present invention. Memory coil 40 is substantially longer than memory coil 36 (FIG. 4) and has sufficient length that when it is inserted in its desired location within the lead, a portion of the coil protrudes proximally from connector pin 18. Memory coil 40 is provided with a central lumen, into which stylet wire 32 (FIG. 2) may be inserted, to straighten curve 42.

Figure 7:
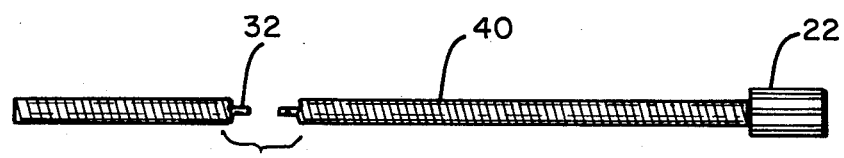
FIG. 7 shows a side plan view of a stylet and the second embodiment of a memory coil, as assembled, according to the present invention.

FIG. 7 shows memory coil 40 as mounted to the stylet of FIG. 2. As shown, stylet wire 32 substantially straightens memory coil 40. The assembly of FIG. 7, like the assembly of FIG. 5, is insertable within the lead of FIG. 1, through the central bore of connector pin 18.

FIG. 8 shows a cutaway view of the lead of FIG. 1. Visible in this view is conductor coil 42, mounted within the lumen of insulative sheath 12. Coil conductor 42 extends from electrode 24 (FIG. 1) to connector pin 18 (FIG. 1). Memory coil 36 and stylet wire 32 are visible inserted within the lumen of conductor coil 42.

In the first embodiment of the present invention, employing the stylet of FIG. 2, the insertion tool of FIG. 3 and the memory coil of FIG. 4, the method of imparting a desired permanent curve to the lead of FIG. 1 is as follows: first, stylet wire 32 is inserted through the central bores of knob 20 and tubular member 34. Second, memory coil 36 is slid over the distal end of stylet wire 32 until the proximal end of memory coil 36 contacts the distal end of tubular member 34. This step straightens memory coil 36, as illustrated in FIG. 5. Third, the assembled stylet insertion tool and memory coil are inserted into the lumen of the lead of FIG. 1. In particular, they are inserted through the central bore of connector pin 18 and advanced through the central lumen of conductor coil 42 until memory coil 36 is located at its desired position, typically the distal end of the lead. The lead may now be introduced into the atrium of a human heart, using standard techniques. Fourth, preferably after introduction of the lead into the atrium, the stylet is removed by means of knob 22, while the insertion tool is held in place in the lead by holding knob 20 stationary relative to connector pin 18. This step allows the lead to display curve 38 of memory coil 36. Finally, the insertion tool is removed from the lead by means of knob 20.

In the second embodiment of the present invention, employing the stylet of FIG. 2 and the memory coil of FIG. 6, the method of imparting a desired permanent curve to the lead of FIG. 1 is as follows: First, stylet wire 32 is inserted in memory coil 36. This step straightens memory coil 36 as shown in FIG. 7. Second, the assembled stylet and memory coil are inserted into the lumen of the lead of FIG. 1. In particular, they are inserted through the central bore of connector pin 18 and advanced through the lumen of conductor coil 42 until memory coil 40 is located in its desired position. The lead may now be introduced into the atrium using known techniques. Fourth, preferably after introduction of the lead into the atrium, the stylet is removed by means of knob 22 while memory coil 40 is retained within the lead by holding the protruding proximal end of coil 40 stationary relative to connector pin 18. This step allows the lead to display curve 42 of memory coil 40. Finally, that portion of the memory coil which protrudes proximal to connector pin 18 is cut off so that the lead may be attached to an implantable pulse generator.

Each of the above discussed embodiments allows for the construction of a pacemaker lead convertible between atrial and ventricular applications, and capable of displaying any desired preset curve. The first embodiment, employing the insertion tool and structural coil of FIG. 4 has as an advantage that it allows for a method of insertion which employs no cutting steps. The lead produced using this embodiment displays a change of flexibility at the proximal end of memory coil 36. In some applications, this may be desirable. In other applications, the embodiment employing the memory coil of FIG. 6 may be more desirable. The lead produced employing this embodiment displays a relatively constant flexibility over the length of the lead, due to the fact that memory coil 40 extends through the entire length of the lead.

This invention has been described in detail with particular reference to preferred embodiments thereof, but it will be understood that variations and modifications can be effected within the spirit and the scope of the invention.

What is claimed is:

1. A body implantable lead, comprising:
   an electrical conductor having a proximal end and a distal end;
   an insulative lead body enclosing said conductor;
   an electrode coupled to the distal end of said conductor;
   curve imparting means tending to assume a predetermined curve, insertable in said lead body for imparting said curve to said lead body;
   straightening means insertable in said lead body for straightening said lead body when said curve imparting means is fully inserted in said lead body; and
   retaining means removably insertable in said lead body for retaining said curve imparting means within said lead body while said straightening means is completely removed from said lead body.

2. A lead according to claim 1, further comprising retaining means for retaining said curve-imparting means within said lead body while said straightening means is removed from said lead body.

3. A lead according to claim 2 wherein said retaining means comprises a tubular member into which said stylet is insertable.

4. A method for imparting a predetermined curve to a body implantable lead, comprising the ordered steps of:
- mounting a curve-imparting means tending to assume said predetermined curve to said lead to a straightening means for straightening said curve-imparting means;
- inserting said curve-imparting means and said straightening means into said lead; and
- completely removing said straightening means from said lead while retaining said curve-imparting means fully inserted within said lead, allowing said curve-imparting means to impart said predetermined curve to said lead.

5. A method according to claim 4, wherein said mounting step further comprises mounting to said straightening means a retaining means, for retaining said curve-imparting means within said lead while said straightening means is removed, and wherein said removing and retaining step further comprises retaining said curve-imparting means within said lead with said retaining means while removing said straightening means, and subsequently removing said retaining means.

6. A body implantable lead, comprising:
- an elongated insulative lead body, having a proximal end and a distal end and tending to assume a generally straight configuration;
- an electrical conductor having a proximal end and a distal end, mounted within said lead body;
- an electrode coupled to the distal end of said conductor;
- an electrical connector coupled to the proximal end of said conductor;
- curve imparting means tending to assume a predetermined curve, insertable within said lead body for imparting said curve to said lead body while said curve imparting means is within said lead body; and
- straightening means, for straightening said lead body insertable within and completely removable from said lead body, while said curve imparting means is fully inserted within said lead body.

7. A lead according to claim 6 wherein said straightening means is removably mountable to said curve imparting means, and straightens said curve imparting means for insertion into said lead body.

8. A body implantable lead according to claim 6 or claim 7, further comprising retaining means for retaining said curve imparting means within said lead body, while said straightening means is removed from said lead body.

9. A lead according to claim 8 wherein said retaining means is removably mountable to sad straightening means, and is insertable within said lead body while mounted to said straightening means.

10. A body implantable lead, according to claim 6, wherein said curve imparting means comprises an elongated memory coil, tending to assume said predetermined curve, and wherein said straightening means comprises stylet means, insertable in said memory coil for straightening said memory coil and for straightening said lead body while said memory coil is inserted in said lead body, said stylet means removable from said lead body and from said memory coil while said memory coil is within said lead body.

11. A lead according to claim 10 further comprising retaining means for retaining said memory coil within said lead body while said stylet means is removed from said lead body.

12. A lead according to claim 11 wherein said retaining means is removably mountable coaxial to said stylet means, locates said memory coil along a predetermined length of said stylet means, and maintains said memory coil at a predetermined location within said lead body during the removal of said stylet means.

13. A body implantable lead, comprising:
- an elongated insulative lead body having a proximal end, a distal end, and a longitudinal lumen having a distal end and a proximal end, said lead body tending to assume a generally straight configuration;
- an electrical conductor mounted within said elongated lead body, having a proximal end and a distal end;
- an electrode coupled to the distal end of said conductor;
- an electrical connector coupled to the proximal end of said conductor;
- a memory coil insertable within the lumen of said lead body, having sufficient length to extend from the distal end of the lumen of said lead to a first point distal to the proximal end of the lumen of said lead body, said memory coil tending to assume a predetermined curve;
- a stylet, having sufficient length to extend from the distal end of the lumen of said lead body to the proximal end of the lumen of said lead body, insertable within said memory coil, tending to assume a generally straight configuration and of sufficient rigidity to straighten said memory coil while inserted in said memory coil; and
- retaining means, mountable to said stylet and of sufficient length to extend from said first point to the proximal end of the lumen of said lead body, for locating said memory coil adjacent the distal end of said stylet, and for retaining said memory coil adjacent the distal end of the lumen of said lead body while said stylet is completely removed from said memory coil.

* * * * *